(12) United States Patent
Fantana et al.

(10) Patent No.: US 8,704,634 B2
(45) Date of Patent: Apr. 22, 2014

(54) SYSTEM FOR CREATING, COLLECTING, STORING AND PROVIDING ACCESS TO DATA FROM AN ELECTRIC POWER DEVICE WHICH CONTAINS A COOLING OR OPERATING LIQUID

(75) Inventors: Nicolaie Fantana, Heidelberg (DE); Oleg Kouzmine, Düsseldorf (DE); Peter Werle, Walsrode (DE); Cornelia Radigk, Halle (DE)

(73) Assignee: ABB Technology AG, Zurich (CH)

( * ) Notice: Subject to any disclaimer, the term of this patent is extended or adjusted under 35 U.S.C. 154(b) by 181 days.

(21) Appl. No.: 13/208,943

(22) Filed: Aug. 12, 2011

(65) Prior Publication Data

US 2012/0044048 A1  Feb. 23, 2012

(30) Foreign Application Priority Data

Aug. 19, 2010  (EP) .................... 10008643

(51) Int. Cl.
 *G05B 19/00* (2006.01)
 *G01N 1/14* (2006.01)

(52) U.S. Cl.
 USPC ..................... 340/5.64; 73/863.83

(58) Field of Classification Search
 USPC ........... 700/231; 340/152, 572.1; 235/472.02; 707/736
 See application file for complete search history.

(56) References Cited

U.S. PATENT DOCUMENTS

| | | | |
|---|---|---|---|
| 5,258,310 A | 11/1993 | Abe et al. | |
| 5,936,715 A * | 8/1999 | Shapanus et al. | 356/70 |
| 6,199,436 B1 | 3/2001 | Morel et al. | |
| 6,271,753 B1 * | 8/2001 | Shukla | 340/545.6 |
| 6,475,443 B1 | 11/2002 | van Deursen et al. | |
| 6,494,617 B1 * | 12/2002 | Stokes et al. | 374/152 |
| 6,879,876 B2 * | 4/2005 | O'Dougherty et al. | 700/231 |
| 7,358,847 B2 * | 4/2008 | Kudo | 340/5.91 |
| 8,477,029 B2 * | 7/2013 | Ashrafzadeh et al. | 340/540 |
| 2004/0148117 A1 * | 7/2004 | Kirshenbaum et al. | 702/82 |
| 2005/0005674 A1 | 1/2005 | Gilbert et al. | |
| 2005/0087255 A1 * | 4/2005 | Humphrey et al. | 141/94 |

(Continued)

FOREIGN PATENT DOCUMENTS

| | | |
|---|---|---|
| DE | 202008014618 U1 | 3/2010 |
| DE | 102008052693 A1 | 4/2010 |

OTHER PUBLICATIONS

European Search Report issued on Mar. 9, 2011 for European Application No. 10008643.8.

*Primary Examiner* — Hai Phan
*Assistant Examiner* — Royit Yu
(74) *Attorney, Agent, or Firm* — Buchanan Ingersoll & Rooney PC

(57) ABSTRACT

A system is provided for creating and/or collecting, storing and providing access to data from an electric power device which contains a cooling or operating liquid. A sensing device is mounted on the electric power device. The sensing device includes a microprocessor/microcontroller, a memory, a display panel, an input panel, and a tag read/write apparatus. A sampling container for holding a liquid sample to be taken from the electric power device has a container tag mounted thereon. The tag read/write apparatus uses a wireless communication link, when a sample has been taken, to transmit (i) administrative data denoting the electric power device, and (ii) diagnosis data denoting the sample taken to the container tag. The diagnosis data can be input directly using the input panel of the sensing device when a sample has been taken.

20 Claims, 2 Drawing Sheets

(56) References Cited

U.S. PATENT DOCUMENTS

| | | |
|---|---|---|
| 2006/0108428 A1* | 5/2006 | Broere .................. 235/472.02 |
| 2006/0251147 A1* | 11/2006 | Balan ........................ 374/152 |
| 2007/0014693 A1* | 1/2007 | Kantrowitz et al. ............ 422/99 |
| 2008/0078827 A1* | 4/2008 | Geiss ......................... 235/375 |
| 2008/0084293 A1* | 4/2008 | Adelbert .................. 340/539.1 |
| 2009/0026907 A1* | 1/2009 | Davidowitz et al. .......... 312/407 |
| 2009/0224923 A1* | 9/2009 | Abraham et al. .......... 340/572.1 |
| 2010/0085161 A1* | 4/2010 | Nishikawa .................. 340/10.3 |
| 2010/0177750 A1* | 7/2010 | Essinger et al. ............. 370/338 |
| 2010/0248213 A1* | 9/2010 | Feiglin ............................ 435/5 |
| 2011/0276570 A1* | 11/2011 | Larsson et al. ............... 707/736 |
| 2012/0025985 A1* | 2/2012 | Bolander et al. .......... 340/572.1 |
| 2012/0186671 A1* | 7/2012 | O'Dougherty et al. ....... 137/551 |

\* cited by examiner

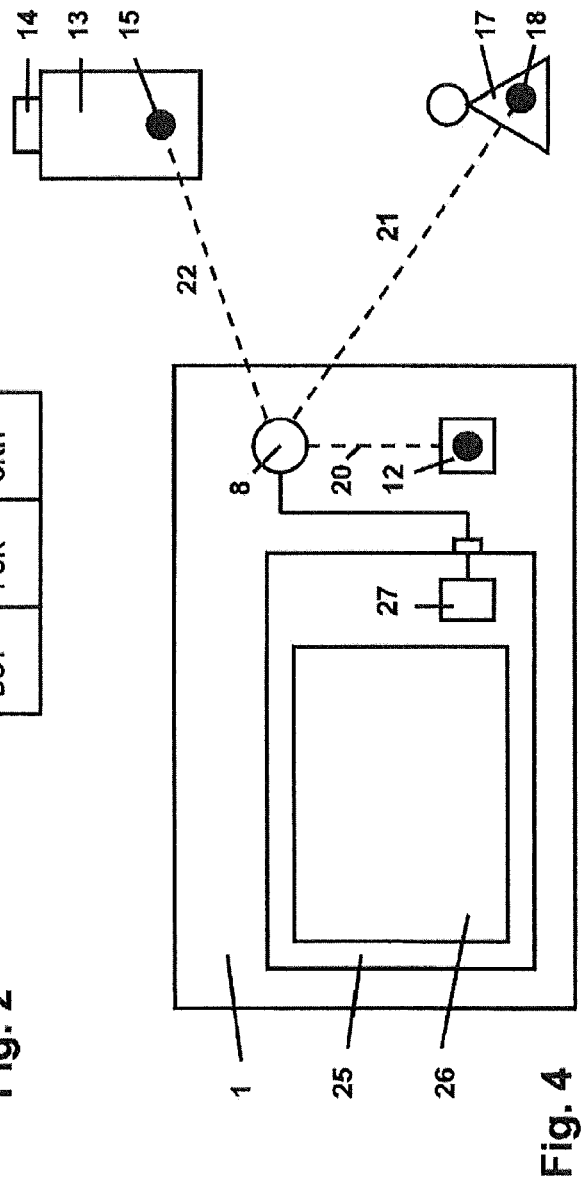
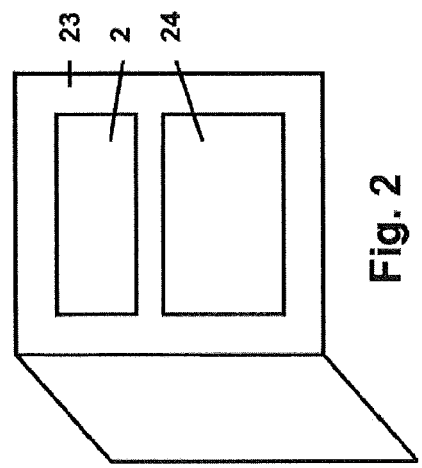

US 8,704,634 B2

SYSTEM FOR CREATING, COLLECTING, STORING AND PROVIDING ACCESS TO DATA FROM AN ELECTRIC POWER DEVICE WHICH CONTAINS A COOLING OR OPERATING LIQUID

RELATED APPLICATION

This application claims priority under 35 U.S.C. §119 to European Patent Application No. 10008643.8 filed in Europe on Aug. 19, 2010, the entire content of which is hereby incorporated by reference in its entirety.

FIELD

The present disclosure relates to a system for creating and/or collecting, storing and providing access to data from an electric power device which contains a cooling or operating liquid.

BACKGROUND INFORMATION

Electric power devices for energy production and industrial power devices may contain cooling liquids or operating liquids, such as oil. An oil-filled power transformer is an example of such an electric power device containing a cooling or operating liquid. To permanently ensure proper operation of the electric power device, a liquid sample is taken from the cooling or operating liquid at particular intervals of time (e.g., during servicing). A sampling container filled with the liquid sample that has been taken is then transported to a remote laboratory, where extensive diagnosis and analysis of the liquid sample can be performed. The sampling container used may either be bottles made of aluminum, steel, glass or plastic, or else syringes or containers which are open at two ends.

In order to record a precise association between the electric power device, on the one hand, and the liquid sample taken, on the other hand, it is known to write down the relevant data, such as the owner and characterizing data of the electric power device, the location at which the sample is taken and desired analysis values, on a sticker or badge which is mounted on the sampling container. In this case, there is the risk of this badge being lost or this sticker being damaged. Furthermore, it is known to provide a container with a container tag which has a read memory area, which can be read by radio and which allows explicit identification of the container.

SUMMARY

An exemplary embodiment of the present disclosure provides a system for creating and/or collecting, storing and providing access to data from an electric power device which contains a cooling or operating liquid. The exemplary system includes a sensing device mounted on the electric power device. The sensing device includes a microprocessor/microcontroller, a memory, a display panel, an input panel, and a tag read/write apparatus. The exemplary system also includes a sampling container configured for holding a liquid sample to be taken from the electric power device, and a container tag mounted on the sampling container. The tag read/write apparatus is configured to use a wireless communication link, when a liquid sample has been taken from the electric power device, to transmit, to the container tag, (i) administrative data denoting the electric power device, and (ii) diagnosis data denoting the sample taken. The input panel of the sensing device is configured to receive an input of the diagnosis data of the liquid sample that has been taken.

BRIEF DESCRIPTION OF THE DRAWINGS

Additional refinements, advantages and features of the present disclosure are described in more detail below with reference to exemplary embodiments illustrated in the drawings, in which:

FIG. 2 shows an installation option for the sensing device according to an exemplary embodiment of the present disclosure;

FIG. 3 shows a specific view of a display panel and input panel according to an exemplary embodiment of the present disclosure; and FIG. 4 shows an exemplary embodiment of the present disclosure with integration of the sensing device into a control, monitoring and/or automation system of the electric power device.

DETAILED DESCRIPTION

Figure 1:
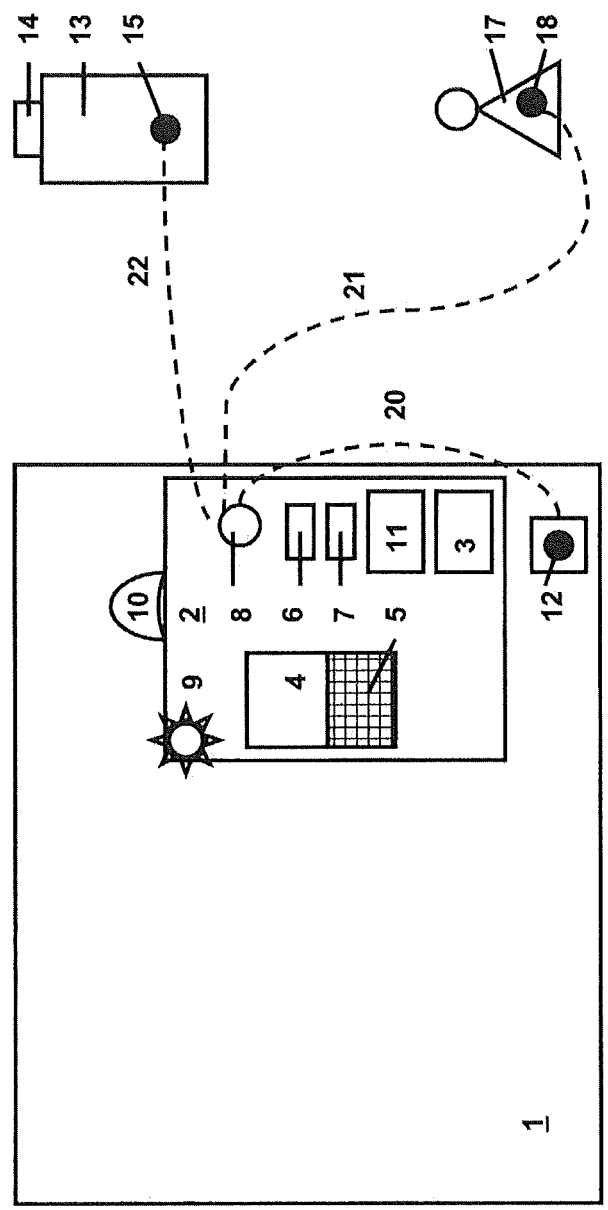
FIG. 1 shows a schematic outline of an exemplary embodiment of the present disclosure with an independent arrangement for creating and/or collecting, storing and providing access to data from an electric power device.

Exemplary embodiments of the present disclosure provide an optimized system for creating and/or collecting, storing and providing access to data from an electric power device which contains a cooling or operating liquid.

An exemplary embodiment of the present disclosure provides a system for creating and/or collecting, storing and providing access to data from an electric power device which contains a cooling or operating liquid. The exemplary system includes a sensing device which is mounted on the electric power device. The sensing device includes a microprocessor/microcontroller, a memory, a display panel, an input panel and a tag read/write apparatus is mounted on the electric power device. The exemplary system also includes a sampling container configured for holding a liquid sample taken from the electric power device. A container tag is mounted on the sampling container. In accordance with an exemplary embodiment, the tag read/write apparatus is configured to use a wireless communication link, when a sample has been taken, to transmit (i) "administrative data" denoting the electric power device, and (ii) "diagnosis data", denoting the sample taken, where the "diagnosis data" can be input directly using the input panel of the sensing device when a sample has been taken, to a container tag.

In accordance with an exemplary embodiment of the system, creating and/or collecting, storing and providing access to data from the electric power device which are related to the taking of a sample do not require any additional mobile computer systems that need to be transported by the servicing person. On the contrary, the data of importance to the sample taken which need to be communicated to the laboratory are available in bundled form after a few "maneuvers" in order to transfer them to the container tag on the sampling container. This results in time-saving and a reduction in the involvement for taking the sample, which provides considerable cost advantages overall. Furthermore, a qualitative improvement is obtained for the servicing of the electric power device.

In accordance with an exemplary embodiment, the sensing device may be integrated in a control, monitoring and/or automation system of the electric power device. In such a configuration, the tag read/write apparatus may be connected to the control, monitoring and/or automation system via a module, as a result of which it is possible to generate and transfer "additional power device data" arising in connection with the monitoring functionality of the system, such as operational values relating to load, temperature and/or current. The tag read/write apparatus then transmits these "additional power device data" using the aforementioned wireless communication link when a sample has been taken.

In accordance with an exemplary embodiment of the system, the tag read/write apparatus can be configured to additionally transmit "historical data", which contain "diagnosis data" ascertained for earlier samples taken and/or resultant "additional power device data", when a sample has been taken.

In accordance with an exemplary embodiment, the tag read/write apparatus and the container tag may be in the form of RFID tags or NFC tags, for example.

In accordance with an exemplary embodiment of the system, the electric power device can have a power device tag mounted therein which stores at least the "administrative data" and is in contact with the sensing device via a communication link (e.g., wired and/or wireless).

In accordance with an exemplary embodiment, there may be a wireless communication link between the tag read/write apparatus and a servicing person tag for identifying the servicing person taking the sample.

FIG. 1 shows a schematic outline of an exemplary embodiment of a system with an independent arrangement for creating and/or collecting, storing and providing access to data from an electric power device. An electric power device 1 for energy production, for example a transformer, can be seen which has oil as a cooling or operating liquid. The electric power device 1 has a sensing device 2 and optionally a power device tag 12 mounted on it. The power device tag 12 may be mounted captively, for example directly, on the transformer tank or otherwise may be situated inside the housing of the sensing device 2.

In accordance with an exemplary embodiment, the sensing device 2 can include the following components:
a microprocessor/microcontroller 3,
a display panel 4,
an input panel 5, which is, for example, in the form of a keypad,
a confirmation key 6 for confirming data/inputs,
a delete key 7 for deleting erroneous data/inputs,
a tag read/write apparatus 8 as a read/write and communication interface,
optionally a visual information signaling element 9, which can be in the form of an LED, for example,
optionally an audible information signaling element 10, and
a memory 11 for storing input/configured data (e.g., a non-transitory computer-readable recording medium, such as a ROM, hard disk drive, optical memory, flash memory, etc.).

In accordance with an exemplary embodiment, the arrangement including the display panel 4, input panel 5, confirmation key 6 and delete key 7 may also be in the form of a touch screen.

In accordance with an exemplary embodiment, the power device tag 12 and the tag read/write apparatus 8 can be in the form of an RFID (Radio Frequency Identification) tag or NFC (Near Field Communication) tag, and are provided with a read/write non-transitory memory. The power device tag 12 may contain the data from the electric power device 1. In addition, in accordance with an exemplary embodiment, the power device tag 12 may contain "historical data", and may also allow explicit identification, for example. In other words, the power device tag 12 stores the "administrative data" and also important events in the past in the form of a "record file". If the distance between the tag read/write apparatus 8 and the power device tag 12 is greater than is usually permissible for RFID tag technology, it is possible for these units 8 and 12 to be additionally in the form of a UHF tag or an active tag or a wireless (radio) sensor node.

The power device tag 12 and the sensing device 2, in this case the tag read/write apparatus 8, are connected to one another via a communication link 20, where the communication link 20 is able to be either wired or wireless (e.g., in RFID form or in UHF form or in the form of active tags or in the form of wireless radio sensor nodes). This communication link 20 can be used to transmit data from the tag read/write apparatus 8 to the read/write memory of the power device tag 12 (e.g., relevant data in connection with a sample which has been taken), and it is conversely possible for data to be transmitted from the power device tag 12 to be transmitted to the tag read/write apparatus 8 (e.g., relevant data for configuration).

FIG. 1 also shows a sampling container 13 for holding a cooling or operating liquid from the electric power device 1. The sampling container 13 is able to be sealed by means of a cap 14 when the liquid sample has been taken from the electric power device 1 and the container 13 has been filled (e.g., partially or fully). In addition, the sampling container 13 includes a container tag 15 which can be in the form of an RFID (Radio Frequency Identification) tag or NFC (Near Field Communication) tag and is provided with a read/write memory. In accordance with an exemplary embodiment, the sampling container 13 can be transported by a servicing person 17, where the servicing person 17 can optionally wear a servicing person tag 18, for example, in the form of an RFID tag or an NFC tag, in order to allow explicit personal identification of that person who has taken a sample of the cooling or operating liquid from the electric power device 1.

In this case, the sampling container 13 can have an associated detachable sensor unit which is mounted detachably on the sampling container 13 at least while the sample is being taken and which has an electronics group including a process unit, an electronic memory circuit and a power supply, a communication group that can be operated by radio and a sensor group, which ascertains provisional "ad-hoc sample sensor system data", such as, for example, the temperature of the liquid sample while it is being taken, in situ while the liquid is being taken.

In accordance with an exemplary embodiment, the system can also include the following features:
an optional (wireless) communication link 21 between the servicing person tag 18 of the servicing person 17 and the tag read/write apparatus 8 in order to enable automatic identification of the servicing person taking the sample, and
a (wireless) communication link 22 between the container tag 15 and the tag read/write apparatus 8 in order to implement the transfer of the data that are relevant to taking a sample to the sampling container 13 and hence ultimately to the remote laboratory.

FIG. 2 shows an exemplary installation option for the sensing device 2. In the illustrated example of the sensing device 2, the electric power device 1 has an equipment cabinet 23 which, besides further power device appliances 24, also holds the sensing device 2, inter alia.

FIG. 3 shows a specific view of an exemplary display panel and input panel. The input panel 5 has nine keys which are arranged in three rows and three columns and are labeled differently, for example, as follows:

the top left key is labeled "TOP", which indicates that the liquid sample has been taken from the top area of the electric power device 1, the middle left key is labeled "MID", which indicates that the liquid sample has been taken from the middle area of the electric power device 1, the bottom left key is labeled "BOT", which indicates that the liquid sample has been taken from the bottom area of the electric power device 1, the top middle key is labeled "DGA" (Dissolved Gas Analysis), which is a request to the laboratory to analyze the gases dissolved in the cooling or operating liquid, the central key is labeled "OIL", which is a request of the laboratory to perform a physical/chemical analysis of the oil, which means, by way of example, that it is requested to examine, inter alia, the viscosity, the acid content, the electrical breakdown voltage, the color, the particles contained, etc., the bottom middle key is labeled "FUR", which is a request to the laboratory to examine the cooling or operating liquid for furans, the top right key is labeled "OK", which indicates that both the electric device 1 and the liquid sample taken are, at first sight, of the proper quality, the middle right key is labeled "REV", which indicates that, at first sight, taking account of the condition of the electric device 1 and/or of the liquid sample taken, it is envisioned to inspect the electric device 1 in the near future, e.g., to replace the cooling or operating liquid, for example, the bottom right key is labeled "CRIT", which indicates that, at first sight, taking account of the condition of the electric device 1 and/or of the liquid sample taken, continued operation of the electric device 1 is no longer possible, for example, because important parts of the electric device 1 are rusty or because cooling or operating liquid is escaping from a point in the electric device.

The display panel 4 is used to display desired data, for example to show the display "Oil taken: Middle Physical/chemical analysis of the oil Result: OK"

after the middle left key "MID", the central key "oil" and the top right key "OK" have been pressed.

FIG. 4 shows an exemplary embodiment of the present disclosure with exemplary integration of the sensing device into a control, monitoring and/or automation system 25 of the electric power device 1. In the illustrated example, the electric power device 1 has a control, monitoring and/or automation system 25 into which the functionalities of some of the components of the sensing device 2 that have been explained above have been effectively integrated, such as the microprocessor/microcontroller 3 and the memory 11. The control, monitoring and/or automation system 25 has a main display panel 26 which is in the form of a touch screen and into which the display panel 4, the input panel 5, the confirmation key 6 and the delete key 7 have been integrated. A module 27 of the control, monitoring and/or automation system 25 is connected to the tag read/write apparatus 8. The functionality of this module 27 is explained in more detail below.

In summary consideration, the functionalities of the exemplary embodiment explained with reference to FIG. 1 with the sensing device 2 in the form of processing components implementing various functional features disclosed herein have been integrated into the control, monitoring and/or automation system 25. In the case of the exemplary embodiment explained with reference to FIG. 4 with the sensing device 2 integrated into the control, monitoring and/or automation system 25, "additional power device data" can be generated, e.g., created/collected and rendered accessible, in comparison with the exemplary embodiment shown in FIG. 1, which data are obtained in connection with the monitoring functionality of the system 25 and are "read" from the system 25 via the aforementioned module 27 and transferred (e.g., by means of a computer processor implementing a software program) to the actual sensing device 2 integrated in the system 25. These "additional power device data" can additionally be transmitted to the sampling container 13 using the wireless communication link 22 in a later step, such as:

operational values such as average values for the load, operational values such as average values for the temperature, operational values such as average values for the current, a number and specification of overloads, an occurrence and specification of "hot spots" (e.g., sections of the electric power device with excessive temperature load), at which prescribed limit values have been exceeded, and/or an indication of current values which have exceeded prescribed limit values.

It should also be added that the above explanations relating to the first embodiment shown in FIG. 1 with the sensing device 2 in respect of the distance between the tag read/write apparatus 8 and the power device tag 12 may also apply in the same way to the exemplary embodiment shown in FIG. 4. In the same way, these units 8 and 12 may additionally be in the form of a UHF tag, an active tag or a wireless sensor node.

The communication link 20 (either wired or wireless, e.g., in RFID form, in UHF form, in the form of active tags, or in the form of wireless sensor nodes) can be used to transmit data from the tag read/write apparatus 8 to the read/write memory of the power device tag 12 (e.g., relevant data in connection with a sample that has been taken), and conversely it is possible for data from the power device tag 12 to be transmitted to the tag read/write apparatus 8 (e.g., relevant data relating to configuration).

The exemplary system is configured for creating and/or collecting, storing and providing access to data from an electric power device. For example, during a configuration phase for the sensing device 2 or for the control, monitoring and/or automation system 25, the functionality of the input panel 5 or of the main display panel 26 is stipulated and permanently stored (in the memory 11), e.g., it is specifically stipulated which key is assigned which label, the functionality of the display panel 4 or of the main display panel 26 is stipulated and permanently stored, e.g., texts to be displayed or symbols to be displayed are stipulated, the "administrative data" from the electric power device 1 are read in, such as explicit identification of the electric power device 1, setup location (e.g., in the form of GPS data) and owner of the electric power device 1, characterizing data from the electric power device 1, such as serial number, power, voltage, etc., and liquid type of the cooling or operating liquid, e.g., oil type.

In this case, the configuration can be performed using the power device tag 12, which contains the "administrative data". A configuration file which is used for the configuration can then be made available, by way of example, using a communication interface of the sensing device 2 or of the control, monitoring and/or automation system 25, for example, in the form of USB interface. A further option is for the servicing person 17 to approach an initialization tag (e.g., RFID tag) of the tag read/write apparatus 8, which initialization tag contains the configuration file that is used for the configuration, whereupon the configuration file is read in. This has the advantage that no additional interface is required. In accordance with an exemplary embodiment, the initialization tag can be prepared/created by a servicing engineer, for example.

The text below provides a more detailed description of the manner of operation of the system for creating and/or collecting, storing and providing access to data from an electric power device:

Step A:

The servicing person 17 takes a sample from the electric power device 1, and the sampling container 13 is filled (e.g., partially or fully) with the sample of the cooling or operating liquid.

Step B:

The servicing person 17 uses the input panel 5, display panel 4 and/or the main display panel 26 to input any of the following "diagnosis data" into the sensing device 2 or the control, monitoring and/or automation system 25:

- the location at which the sample was taken from the electric power device 1, for example, "in the base area", "in the top area", "in the middle area", "tap xxx",
- the date and time at which the sample was taken,
- the amount of the liquid sample taken,
- the name of the servicing person 17 who took the liquid sample,
- optionally, an explicit confirmation code produced while the sample was being taken,
- important (for example, critical) observations or comments from the servicing person 17 while the liquid sample is being taken,
- basic observations that can be identified by the servicing person 17 at first glance, such as "oil condition: OK", "oil condition: inspection required" or "oil condition: critical", as explained above,
- the desired analysis values to be ascertained by the remote laboratory, for example, gases dissolved in the liquid (e.g., dissolved hydrogen), chemical tests to be performed, furans, etc., including, inter alia,
    - acetylene content,
    - ethyne content,
    - water content,
    - carbon monoxide content,
    - carbon dioxide content,
    - oxygen content,
    - nitrogen content,
    - ascertained conductivity,
    - ascertained acid content.

In accordance with an exemplary embodiment, the servicing person can press a key from the left row, a key from the middle row and a key from the right row, as explained above with reference to FIG. 4.

The name of the servicing person 17 who took the liquid sample can alternatively be input automatically and directly using the communication link 21 between the servicing person tag 18 and the tag read/write apparatus 8.

Step C:

The servicing person 17 brings the sampling container 13 close to the tag read/write apparatus 8. The wireless communication link 22 is used to automatically transmit the following data from the tag read/write apparatus 8 to the container tag 15 of the sampling container 13:

- the "administrative data" detailed above,
- the "diagnosis data" detailed above,
- the "additional power device data" detailed above,
- optionally the "diagnosis data" and/or "additional power device data" ascertained in the past (when earlier samples were taken), also called "historical data".

The visual information signaling element 9 and/or the audible information signaling element 10 provide assistance for the steps explained above. For example, visual and/or audible means are used to notify the servicing person 17 of "Ready", "Finished", "Error" etc. signals in order to facilitate menu guidance.

In a step D, the sampling container 13 can then be transported to the laboratory, where the detailed diagnosis and analysis of the liquid sample taken are performed in accordance with the information stored in the container tag 15.

As already indicated above, the tag read/write apparatus 8 can, when a sample has been taken, transmit relevant data to the power device tag 12 in a step E (update), such as the date on which the sample was taken and comments relating to critical variables. These updated data are then available again when the next sample is taken.

In this context, the "historical data" ascertained in the past which are stored in the memory 11 of the sensing device 2 can be compared with the present "diagnosis data" and/or "additional power device data" and related to one another. Appropriate combination of the individual data from the liquid samples taken produces an overall picture representing the present condition of the electric device 1 and this can be used to infer proposed measures which allow the electric device 1 to be operated safely in the future too. Trends can be identified in good time, with, for example, risk assessments, fuzzy logic, "neural networks" etc. being able to be used. Visual display using the display panel 4 or main display panel 26 is possible, as explained above.

In addition to the explanations above, it should be added that the sensing device 2 or the control, monitoring and/or automation system 25 may additionally have a voice output for outputting information for the user (e.g., the servicing person 17). Furthermore, a voice input may be provided as an alternative or in addition to the input panel 5, display panel 4 and/or main display panel 26 in order to provide the user with the option of making voice inputs, for example, the inputs explained with reference to FIG. 4 can be made in the form of voice inputs in such a case.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

LIST OF REFERENCE SYMBOLS

1 Electric power device, e.g., transformer
2 Sensing device
3 Microprocessor/microcontroller
4 Display panel
5 Input panel
6 Confirmation key
7 Delete key
8 Tag read/write apparatus
9 Visual information signaling element
10 Audible information signaling element
11 Memory
12 Power device tag
13 Sampling container for a cooling or operating liquid 14 Cap
15 Container tag
17 Servicing person
18 Servicing person tag
20 Communication link between power device tag 12 and sensing device 2 (e.g., wired or wireless)
21 Communication link between servicing person tag and tag read/write apparatus (e.g., wireless)
22 Communication link between tag read/write apparatus and container tag (e.g., wireless)
23 Equipment cabinet
24 Power device appliances
25 Control, monitoring and/or automation system
26 Main display panel
27 Module

What is claimed is:

1. A system for at least one of creating and collecting data from an electric power device which contains a cooling or operating liquid, and storing and providing access to the data, the system comprising:
a sensing device mounted on the electric power device, the sensing device including a microprocessor/microcontroller, a memory, a display panel, an input panel, and a tag read and write apparatus;
a sampling container configured for holding a liquid sample to be taken from the electric power device;
a container tag mounted on the sampling container, the container tag including a detachable sensor unit configured to measure a temperature of the liquid sample when the liquid sample has been taken; and
a remote laboratory unit,
wherein the tag read and write apparatus is configured to use a wireless communication link, when a liquid sample has been taken from the electric power device, to transmit, to the container tag, (i) administrative data denoting the electric power device, and (ii) diagnosis data denoting the sample taken, the diagnosis data containing at least one of comments and observations about the temperature of the liquid sample that has been taken;
wherein the input panel of the sensing device is configured to receive an input of the diagnosis data of the liquid sample that has been taken,
wherein the sensor unit of the container tag is configured to store the administrative data and diagnosis data transmitted to the container tag, and
wherein the container tag is configured to transmit the administrative data and diagnosis data to the remote laboratory unit when the sampling container is transported to the remote laboratory unit to enable a detailed diagnosis of the liquid sample based on the administrative data and diagnosis data stored in the container tag.

2. The system according to claim 1, wherein the electric power device comprises a control, monitoring and automation system, and the sensing device is integrated in the control, monitoring and automation system.

3. The system according to claim 2, wherein the tag read and write apparatus is connected to the control, monitoring and automation system via a module comprised in the electric power device, and
wherein the control, monitoring and automation system is configured to generate additional power device data arising in connection with monitoring of functionality of the control, monitoring and automation system, and the tag read and write apparatus is configured to transfer the generated additional power device data to the container tag.

4. The system according to claim 3, wherein the tag read and write apparatus is configured to transmit the additional power device data to the container tag using the wireless communication link when a sample has been taken.

5. The system according to claim 4, wherein the tag read and write apparatus is configured to transmit historical data, which contain at least one of (i) diagnosis data ascertained for earlier samples taken, and (ii) resultant additional power device data, when a sample has been taken.

6. The system according to claim 1, wherein the tag read and write apparatus and the container tag are each in the form of RFID tags.

7. The system according to claim 1, wherein the tag read and write apparatus and the container tag are each in the form of NFC tags.

8. The system according to claim 1, wherein the sensing device is installed in an equipment cabinet.

9. The system according to claim 1, wherein the electric power device comprises a power device tag mounted thereon,
wherein the power device tag is configured to store the administrative data and previous important events as a record file, and is in contact with the sensing device via a communication link.

10. The system according to claim 1, comprising:
a wireless communication link between the tag read and write apparatus and a servicing person tag for identifying the servicing person taking the sample.

11. The system according to claim 3, wherein additional power device data includes operational values relating to at least one of a load, temperature and current.

12. The system according to claim 3, wherein the tag read and write apparatus and the container tag are each in the form of RFID tags.

13. The system according to claim 3, wherein the tag read and write apparatus and the container tag are each in the form of NFC tags.

14. The system according to claim 4, wherein the tag read and write apparatus and the container tag are each in the form of RFID tags.

15. The system according to claim 4, wherein the tag read and write apparatus and the container tag are each in the form of NFC tags.

16. The system according to claim 5, wherein the tag read and write apparatus and the container tag are each in the form of RFID tags.

17. The system according to claim 5, wherein the tag read and write apparatus and the container tag are each in the form of NFC tags.

18. The system according to claim 5, wherein the electric power device comprises a power device tag mounted thereon,
wherein the power device tag is configured to store the administrative data and previous important events as a record file, and is in contact with the sensing device via a communication link.

19. The system according to claim 5, comprising:
a wireless communication link between the tag read and write apparatus and a servicing person tag for identifying the servicing person taking the sample.

20. The system according to claim 9, comprising:
a wireless communication link between the tag read and write apparatus and a servicing person tag for identifying the servicing person taking the sample.

* * * * *